United States Patent [19]

Horwitz et al.

[11] 4,169,011

[45] Sep. 25, 1979

[54] FACILE SYNTHESIS OF 3'-PHOSPHOADENOSINE 5'-PHOSPHOSULFATE (PAPS)

[75] Inventors: Jerome P. Horwitz; John P. Neenan; Radhey S. Misra; Jurij Rozhin; Anne L. Huo, all of Detroit, Mich.; Kirsten D. Philips, deceased, late of Detroit, Mich., by Judson C. Philips, administrator

[73] Assignee: The United States of America as represented by the Department of Health, Education and Welfare, Washington, D.C.

[21] Appl. No.: 840,783

[22] Filed: Oct. 11, 1977

[51] Int. Cl.$^2$ .......................................... C12D 13/06
[52] U.S. Cl. .............................................. 435/72
[58] Field of Search ................................. 195/28 N

[56] References Cited

U.S. PATENT DOCUMENTS 3,268,416  8/1966  Igarasi et al. ................. 195/28 N

OTHER PUBLICATIONS

Cherniak, et al., J. Biol. Chem. 239:2986–2990 (1964).

Simonscits, et al., Biochim. Biophys. Acta 395:74–79 (1975).
Rozhin et al., J. Biol. Chem. 249:2079–2087 (1974).
Horwitz et al., Biochim. Biophys. Acta, 480:376–381 (1977).

Primary Examiner—Alvin E. Tanenholtz
Attorney, Agent, or Firm—John S. Roberts, Jr.

[57] ABSTRACT

3'-Phosphoadenosine 5'-phosphosulfate, also known as PAPS, is useful in establishing sulfate transfer mechanisms in animals and may be produced by a chemical process yielding 68–72% product from a pure adenosine 2',3'-cyclic phosphate 5'-phosphate, which compound is initially prepared from the reaction of adenosine and pyrophosphoryl chloride. In the present procedure the pure cyclic phosphate is reacted with triethylamine-N-sulfonic acid to produce 2',3'-cyclic phosphate 5'-phosphosulfate. Subsequently, by hydrolysis with the enzyme ribonuclease-T$_2$, the desired compound is produced. Alternatively, the 2'-phosphoadenosine 5'-phosphosulfate, known as iso-PAPS, may be produced from 2',3'-cyclic phosphate 5'-phosphosulfate by treatment with a different enzyme, PDase or spleen phosphodiesterase. This latter compound, iso-PAPS, biologically has only one-third the activity of PAPS, the natural isomer.

4 Claims, No Drawings

FACILE SYNTHESIS OF 3'-PHOSPHOADENOSINE 5'-PHOSPHOSULFATE (PAPS)

The present invention relates to a practical chemical synthesis of 3'-phosphoadenosine 5'-phosphosulfate

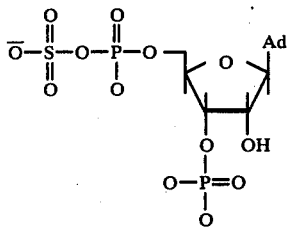

in yields of 68–72% from adenosine 2', 3'-cyclic phosphate 5'-phosphate

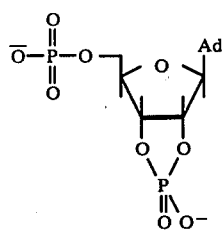

which is designated the starting material for this process. Compound II may be conveniently prepared by reacting adenosine

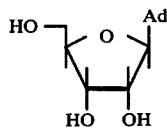

with pyrophosphoryl chloride under hydrolysis conditions at pH 7.5 to provide a pure starting material. Reaction of II with triethylamine-N-sulfonic acid affords adenosine 2', 3'-cyclic phosphate 5'-phosphosulfate

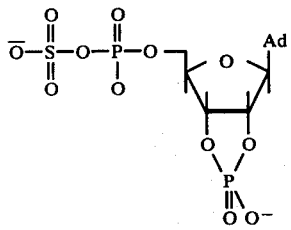

which, on treatment with ribonuclease $T_2$-RNase, provides the desired compound, 3'-phosphoadenosine 5'-phosphosulfate (PAPS) (IV).

The iso or II isomer may be prepared by treating III with spleen phosphodiesterase (PDase) which converts III to the 2'-phosphoadenosine 5'-phosphosulfate

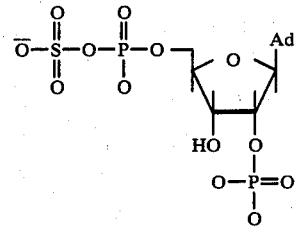

The biological activity of IV (PAPS) may be measured by sulfate transfer to [6,7-$^3$H$_2$]estrone as mediated by bovine adrenal estrone sulfotransferase (3'-phosphoadenylylsulfate: estrone 3-sulfotransferase, EC 2.8.2.4) and is identical with that obtained with a sample of IV prepared by an established biochemical procedure. By the same contrast, V exhibits approximately one-third the activity of the natural isomer.

The Roman numerals designated above correspond with those of the schematic below.

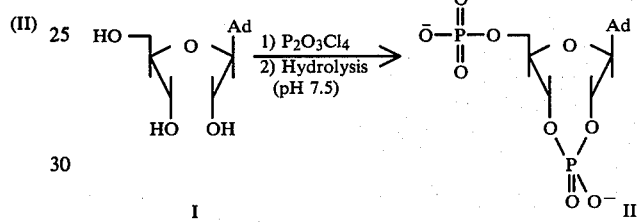

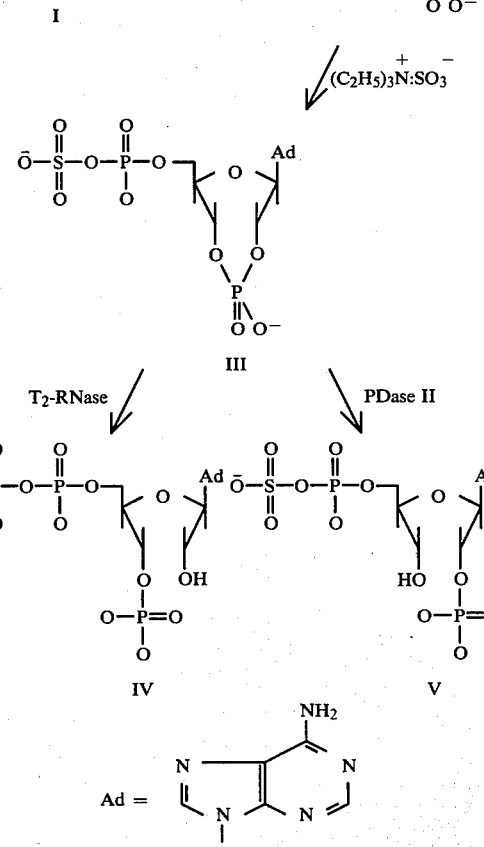

The biological test data is in keeping with the fact that it is well established that PAPS is the sulfate donor in the formation of sulfate esters of a wide range of biological compounds found in nature for which a corresponding spectrum of sulfotransferases of differing specificities are needed for sulfation of such diversified types of substrates as phenols, steroids, N-arylhydroxylamines and glycosides. The source of active surface in these transfer reactions is in all cases 3'-phosphoadenosine 5'-phosphosulfate (IV).

Until now the pursuit of specificity studies of the sulfotransferases has been handicapped by the lack of a suitable synthesis to provide an adequate supply of pure IV. It is noted that enzymic preparations of active sulfate from adenosine triphosphate (ATP) are tedious, time-consuming and convenient for only very small quantities. The present process describes an expeditious approach to pure IV (PAPS) and additionally may be utilized for the synthesis of analogs of IV, such as those proceeding from guanosine or cytidine. Some additional analogs of PAPS in which the present process may be applied are 8-bromo-3'-phosphoadenosine 5'-phosphosulfate, 3'-phosphoinosine 5'-phosphosulfate, 3'-phosphonebularine 5'-phosphosulfate, 3'-phosphotubercidin 5'-phosphosulfate, 2'-phosphotubercidin 5'-phosphosulfate and 3'-phosphoformycin 5'-phosphosulfate.

PRIOR ART

J. P. Horwitz, et al, *Biochim. Biophys. Acta,* 480:376–381 (1977)—a journal review illustrating the procedure of the present application.

R. Cherniak and E. A. Davidson, *J. Biol. Chem.,* 239:2986–2990 (1964)—a production of PAPS by a chemical process which at the key II position produces either 2', 5'-diphosphate or its positional isomer adenosine 3', 5'-diphosphate or a mixture of both; i.e., adenosine 2'(3'), 5'-diphosphate, and there is produced a product which yields PAPS, as stated, as 43% overall. Additionally, at page 2988, column 2, the statement is made as follows: "The presence of about 5% of the corresponding 2' isomer was indicated by analysis with 3'-nucleotidase and acid hydrolysis". This indicates a difference in the purity of the cyclic phosphate reactant as well as in the PAPS product which in Cherniak is contaminated with the isomer iso-PAPS. The separation and elution procedures using Cherniak are involved and time consuming.

A. Simonscits and J. Tomasz, *Biochim. Biophys. Acta,* 395:74–79 (1975)—a teaching is made of the use of pyrophosphoryl chloride in production of cyclic phosphate or in the present reaction I →II.

J. Rozhin et al, *J. Biol. Chem.,* 249:2079–2087 (1974)—testing to show that in estrogen structural changes in all four rings of the estratriene nucleus affected sulfation and testing of PAPS or 3'-phosphoadenosine 5'-phosphosulfate.

As contrasted with the prior art above, the present process, which for practical purposes starts from a pure cyclic phosphate obtains yields in the range 68–72% from adenosine 2', 3'-cyclic phosphate 5'-phosphate. This compound is purified in the present process on a column of DEAE Sephadex A-25 using a linear gradient of triethylammonium bicarbonate to elute the product II. The purity and exclusivity are the keys to the present process and fulfill an awaited chemical synthesis of PAPS over the previous small quantity biochemical procedures. In this process a highly purified reactant minimizes the side effects which previously made the production less than successful. In the production of PAPS (IV), the biological activity measured by sulfate transfer to [6,7-$^3$H$_2$]estrone as mediated by bovine adrenal estrone sulfotransferase is identical with that obtained with IV prepared by an established biochemical procedure. In contrast, iso-PAPS (V) exhibits approximately one-third the activity of the natural isomer IV. Additionally, the isolation of intermediate III allows flexibility in this process to produce PAPS (IV) and analogs as well as the positional isomer V, depending on the choice of enzyme treatment; i.e., T$_2$ RNase of PDase.

GENERALIZED PROCEDURE

The phosphorylation of adenosine (I) with pyrophosphoryl chloride followed by neutral buffered hydrolysis (cf. Simonscits and Tomasz, supra.) provides a convenient route to adenosine 2', 3'-cyclic phosphate 5'-phosphate (II). Purification of II was achieved in the present invention by DEAE-Sephadex A-25 column chromatography using a linear gradient of triethylammonium bicarbonate (TEAB), pH 7.5 which afforded II in 62% yield.

The formation of the 5'-sulfatophosphate anhydride moiety (III) was effected with triethylamine-N-sulfonic acid. The requisite separation of III from the sulfating agent and trioctylamine was readily accomplished on a column of Sephadex G-10 and elution with TEAB. Subsequent treatment of III with ribonuclease T$_2$ gave IV in yields of 68–72% (based on II) following column chromatography on DEAE-Sephadex A-25. The detection of 22% of adenosine 2'(3'),5'-diphosphate indicates that the conversion of II to III was in the order of 90%. A different enzyme PDase II hydrolyzed adenosine 2',3'-cyclic phosphate 5'-sulfatophosphate (III) to V.

In agreement with the assigned structures it was found that acidic treatment of IV gave adenosine 3',5'-diphosphate with no chromatographic indication in either S$_1$ or S$_2$ of the presence of the 2',5'-isomer. The same conditions of hydrolysis applied to V gave adenosine 2',5'-diphosphate as the sole product.

Biological activity of IV and V was determined by sulfate transfer to [6,7$^3$H$_2$]estrone in the presence of bovine adrenal estrogen sulfotransferase (E.C. 2.8.2.4). The activity of IV was virtually identical to that obtained with a sample of PAPS derived via the enzymatic procedure. By varying the concentration of IV between 15–100 μM and with [6,7-$^3$H$_2$]estrone maintained at 100 μM, saturation curves for IV from two sources were produced which were essentially superimposable. Iso-PAPS exhibited approximately one-third per cent the activity of the natural isomer. Moreover, V showed fractional inhibition of estrone-sulfation (by IV) of 0.33 (unity=100% sulfation).

The availability of adenosine 2',3'-cyclic phosphate 5'-phosphate (II) provides ready access to IV and V via III. The use of Sephadex G-10 column chromatography provides a facile and rapid separation of III from tri-n-octylamine and triethylamine-N-sulfonic acid. Enzymatic cleavage of the 2',3'-cyclic phosphate ester in III can be achieved to afford either IV or V using the requisite enzyme. Final purification of the products is conveniently effected on DEAE-Sephadex A-25 employing linear gradient elution of the column by TEAB.

EXAMPLES

General Procedure

Bovine spleen phosphodiesterase II (E.C. 3.1.4.18) and ribonuclease T$_2$ were purchased from Sigma Chemical Company. Bovine adrenal estrogen sulfotransferase (E.C. 2.8.2.4.) was isolated and purified as described by Adams et al, *Biochim. Biophys. Acta.*, 370:160–188 (1974). [$^{35}$S]PAPS and [6,7-$^3$H$_2$]-estrone were purchased from New England Nuclear Corp.

Thin-layer chromatography was performed in System S$_1$: saturated (NH$_4$)$_2$ SO$_4$/0.1 M ammonium acetate/2-propanol (79:19;2, v/v), and in System S$_2$:1-propanol/conc. NH$_4$OH/H$_2$O (6:3:1, v/v) on pre-coated cellulose sheets (Polygram Cel 300 UV$_{254}$, Machery Nagel). Paper electrophoresis was performed in a Savant high voltage electrophoresis apparatus on Whatman No. 1 paper in Solvent E$_1$:0.02 M Na$_2$HPO$_4$, pH 7 at 30 V·cm$^{-1}$ for 1.5 h. Thin-layer electrophoresis was performed in a Brinkmann Desaga apparatus on pre-coated cellulose F plates (E. Merck) in Solvent E$_2$: 0.025 M sodium citrate, pH 5.4 at 15 V·cm$^{-1}$ for 2 h. R$_F$ values and electrophoretic mobilities are summarized in Table I.

TABLE I

Thin-Layer Chromatography and Electrophoresis of Compounds

| Compound | R$_F$ S$_1$ | R$_F$ S$_2$ | Mobility* E$_1$** | Mobility* E$_2$*** |
|---|---|---|---|---|
| Adenosine 5'-phosphate | — | — | 0.58 | 0.19 |
| II | 0.33 | 0.32 | 0.82 | 0.72 |
| III | 0.33 | 0.48 | 0.99 | — |
| Adenosine 3',5'-diphosphate | 0.50 | 0.15 | 0.85 | 0.59 |
| IV | 0.53 | 0.27 | 1.00 | 1.00 |
| V | 0.56 | 0.24 | 1.00 | 1.08 |
| Adenosine 2',5'-diphosphate | 0.59 | 0.15 | 0.85 | — |

*Relative to mobility of Compound IV.
**Paper electrophoresis.
***Thin-layer electrophoresis.

EXAMPLE 1

Preparation of Adenosine 2',3'-cyclic phosphate 5'-phosphate chromatographed C. on a This compound was prepared from adenosine (Compound I, 0.67 g, 2.5 mmol) using about 2.5 mmol of pyrophosphoryl chloride in tenfold relationship to adenosine at 0°–3° C. with stirring and without moisture by a modification of the method of Simoncsits and Tomasz, supra. After hydrolysis of the reaction mixture with 1.0 M triethylammonium bicarbonate at a pH 7.5 below 10° C., the buffer was removed by concentration to a small volume, followed by several evaporations with ethanol under reduced pressure at 30° C. The white residue was dissolved in 37.5 ml of 0.05 M triethylammonium bicarbonate and stored at −15° C. A 6 ml portion of the crude product (5525 A$_{259}$ units, one A$_{259}$ unit is that amount of material in 1 ml of solution that has an absorbance of 1.0 when it is measured with a 1.0 cm optical path at 259 nm) was chromatographed at 4° C. on a 2.5·35 cm column of DEAE-Sephadex A-25 with a linear gradient of 2 l each of 0.05–1.0 M triethylammonium bicarbonate, pH 7.5. Fractions (approx. 20 ml each) 78–97 contained 3800 A$_{259}$ units (62% yield, based on adenosine and $\epsilon_{max}^{H2O}$=15 400 for AMP) of Compound II. The buffer was removed in the usual manner and the product was frozen for storage in 5 ml of H$_2$O.

EXAMPLE 2

Preparation of adenosine 2', 3'-cyclic phosphate 5'-phosphosulfate (Compound III)

To a solution of 2890 A$_{259}$ units of Compound II in 9.1 ml of ethanol was added 0.34 ml of trioctylamine. The ethanol was removed under reduced pressure and the residue was rendered anhydrous by repeated evaporation from dimethylformamide at the oil pump. To the residue was added 3 ml of dimethylformamide, 3 ml of dioxane and 0.6 ml of pyridine and the mixture was shaken for 5 min. Then, 110 mg of triethylamine-N-sulfonic acid (high oral toxicity) was added and the reaction mixture was sealed and shaken overnight at room temperature. A thin-layer chromatogram in S$_2$ indicated that the major product was Compound III. The solvents were removed at the oil pump and the residue and suspended in 6 ml of ice-cold H$_2$O containing 0.2 ml of 1.5 M NH$_4$OH. The mixture was adjusted to pH 7 and applied to a Sephadex G-10 column (2.6·40 cm), which had been pre-equilibrated at room temperature with 0.1 M triethylammonium bicarbonate in 20% ethanol. Elution was continued until 60 ml had been collected. Six 20 ml fractions then were collected and fractions 1–4 were pooled to give 2880 A$_{259}$ units. Buffer was removed in the usual manner. To the residue was added 5 ml of ice-cold H$_2$O and the pH was adjusted to 5.9 with 1.5 M NH$_4$OH. Crude Compound III was used in the enzymatic transformations without further purification.

EXAMPLE 3

Preparation of 3'-phosphoadenosine 5'-phosphosulfate (Compound IV)

To the solution of Compound III was added 0.2 ml (100 units) of an aqueous solution of ribonuclease T$_2$. After 20 h at room temperature a thin-layer chromatogram in System S$_2$ showed complete conversion of Compound III to Compound IV (cf Table I, supra). Chromatography on DEAE-Sephadex A-25 in the manner described for Compound II (Example 1) gave three major peaks. Peak 1 (fractions 104–122) contained 623 A$_{259}$ units (22%) of adenosine, 3',5'-diphosphate ($\lambda_{max}^{H2O}$=259 nm). Peak 2 (fractions 140–159) contained 1932 A$_{259}$ units (68%) of Compound IV. Peak 3 (fractions 166–180) contained 196 A$_{259}$ units (7%) of an unidentified compound, which exhibited an anomalous ultraviolet spectrum ($\lambda_{max}^{H2O}$=262 nm).

Fractions containing Compound IV were pooled and the buffer was removed in the usual manner. The product was redissolved in approx. 3 ml of H$_2$O and the solution was adjusted to pH 7 with dilute NH$_4$OH. Treatment of a small aliquot of the latter with an equal volume of 0.2 M HCl at 37° C. for 1.75 h gave adenosine 3',5'-diphosphate as the sole detectable product in Systems S$_1$ and S$_2$. Compound IV was homogeneous in S$_1$, S$_2$, E$_1$ and E$_2$. It exhibited a typical adenine nucleotide spectrum ($\lambda_{max}^{H2O}$=259 nm, $\lambda_{min}^{H2O}$=227), and it could be frozen for storage or kept indefinitely in 50% ethanol at −20° C. Compound IV gave yields of 68–72% based on Compound II. Consonant with the assigned structures, it was found that acidic treatment of Compound IV gave adenosine 3',5'-diphosphate with no indication of the presence of the 2',5'-isomer.

EXAMPLE 4

Preparation of 2'-phosphoadenosine 5'-phosphosulfate (Compound V)

To a solution of 790 A$_{259}$ units of crude Compound III in 2 ml of H$_2$O, adjusted to pH 6 with 1.5 M NH$_4$OH, was added 0.4 ml (9 units) of a solution of spleen phosphodiesterase II in 0.05 M potassium acetate, pH 6. After 18 h at room temperature, chromatography in S$_1$ and S$_2$ showed approx. 40% formation of Compound V. An additional 4.5 units of enzyme were added and the mixture was kept at room temperature for 18 h to complete the reaction. Compound V was isolated in 89% yield following chromatography on DEAE-Sephadex A-25 in the usual manner. It was homogeneous in $S_1$, $S_2$, $E_1$ and $E_2$ and exhibited a typical adenine nucleotide spectrum ($\lambda_{max}$ =259 nm, $\lambda_{min}$=227 nm). It moved slightly faster than Compound IV in $S_1$ and $E_2$ but had nearly the same mobility as Compound IV in Systems $S_2$ and $E_1$. After adjustment of pH to 7, Compound V was frozen for storage at −15°. Hydrolysis of Compound V under acid conditions gave adenosine 2′,5′-diphosphate as the sole product and the biological activity as compared with the natural isomer IV was about 33%.

EXAMPLE 5

Comparative sulfation of estrone by Compounds IV and V

Sulfation of estrone with synthetic Compound IV (PAPS) was determined using the procedure described in the article by Roshin et al, ante. Sulfation by Compound V was as follows. The ability of Compound V to donate its sulfate to estrone was determined with [6,7-$^3H_2$]estrone (1.3·10$^6$ dpm/4 nmol) by modification of the above-mentioned Rozhin et al method in which Compound V (0.11 mM) is now substituted for Compound IV.

After termination of the incubation, excess free [$^3$H]estrone was extracted three times with 0.3 ml of ethyl ether and the aqueous sample adjusted to 0.5 ml with redistilled methanol. An aliquot (25 μl) was applied, together with 15 μg of methanolic estrone sulfate marker, to type SG chromatography media (Gelman Instrument Co., Ann Arbor, Mich.) and developed with chloroform/acetone/acetic acid (110:35:6). Estrone sulfate was visualized by spraying with methylene blue and the spot punched out with a cork borer and counted in 10 ml of Bray's dioxane scintillation solution. Methylene blue did not affect counting efficiency. The amount of steroid sulfate ester produced was calculated utilizing the specific activity of [$^3$H]estrone.

The effect of Compound V as an inhibitor of estrogen sulfotransferase was determined by adding the inhibitor (0.1 mM) to an incubation mixture containing 22 μM Compound IV and [6,7-$^3H_2$]estrone (1.3·10$^6$ dpm/22 nmol). Results are expressed as fractional inhibition.

I claim:

1. The preparation of 3′-phosphoadenosine 5′-phosphosulfate (IV) by a process which comprises reacting adenosine (I) with pyrophosphoryl chloride to produce pure adenosine 2′,3′-cyclic phosphate 5′-phosphate (II) and subsequently reacting said cyclic phosphate (II) with triethylamine-N-sulfonic acid to produce adenosine 2′,3′-cyclic phosphate 5′-phosphosulfate (III) and treating (III) with the enzyme ribonuclease-$T_2$ to produce the desired 3′-phosphoadenosine 5′-phosphosulfate (IV).

2. The preparation of 2′-phosphoadenosine 5′-phosphosulfate (V) by a process which comprises reacting adenosine (I) with pyrophosphoryl chloride to produce pure adenosine 2′,3′-cyclic phosphate 5′-phosphate (II) and subsequently reacting said cyclic phosphate (II) with triethylamine-N-sulfonic acid to produce adenosine 2′,3′-cyclic phosphate 5′-phosphosulfate (III) and treating (III) with the enzyme spleen PDase to produce 2′-phosphoadenosine 5′-phosphosulfate (V).

3. The process according to claim 1 wherein the pyrophosphoryl chloride is substantially pure pyrophosphoryl chloride.

4. The process according to claim 2 wherein the pyrophosphoryl chloride is substantially pure pyrophosphoryl chloride.

* * * * *

UNITED STATES PATENT OFFICE
CERTIFICATE OF CORRECTION

Patent No. 4,169,011    Dated Sept. 25, 1979

Inventor(s) Jerome P. Horwitz et al

It is certified that error appears in the above-identified patent and that said Letters Patent are hereby corrected as shown below:

Column 2, lines 25-58, formulas I, II, III, IV, & V

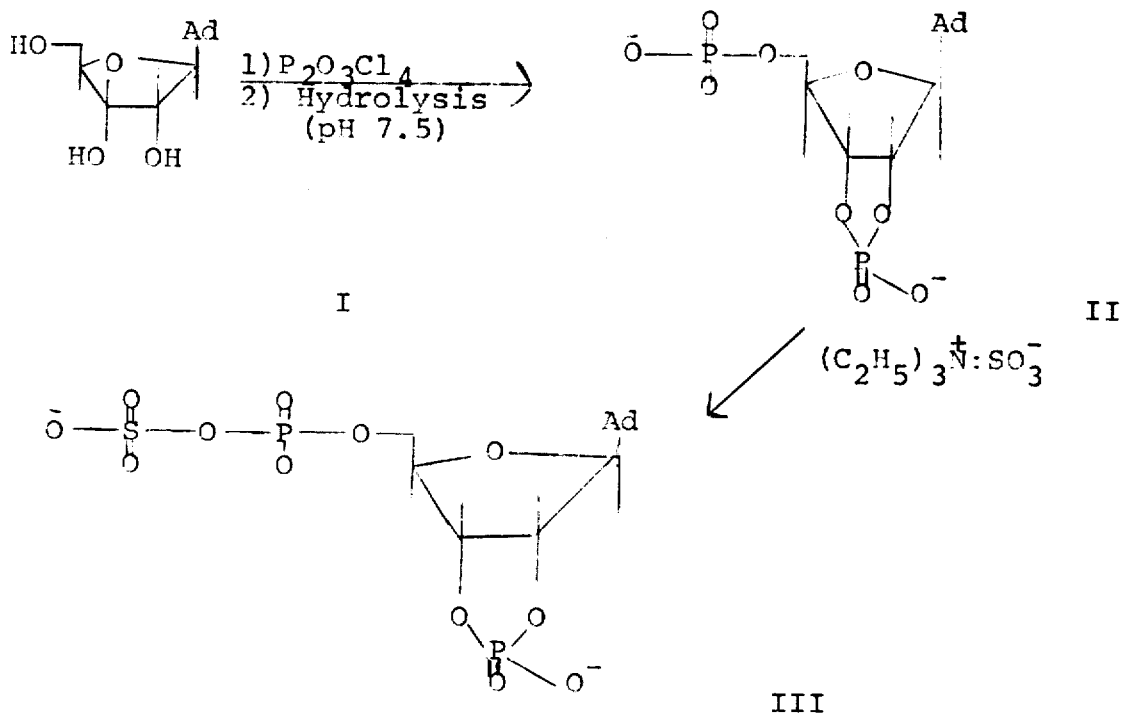

UNITED STATES PATENT OFFICE
CERTIFICATE OF CORRECTION

Patent No. 4,169,011    Dated Sept. 25, 1979

Inventor(s) Jerome P. Horwitz et al

It is certified that error appears in the above-identified patent and that said Letters Patent are hereby corrected as shown below:

Column 2, lines 25-58, formulas I, II, III, IV & V (cont)

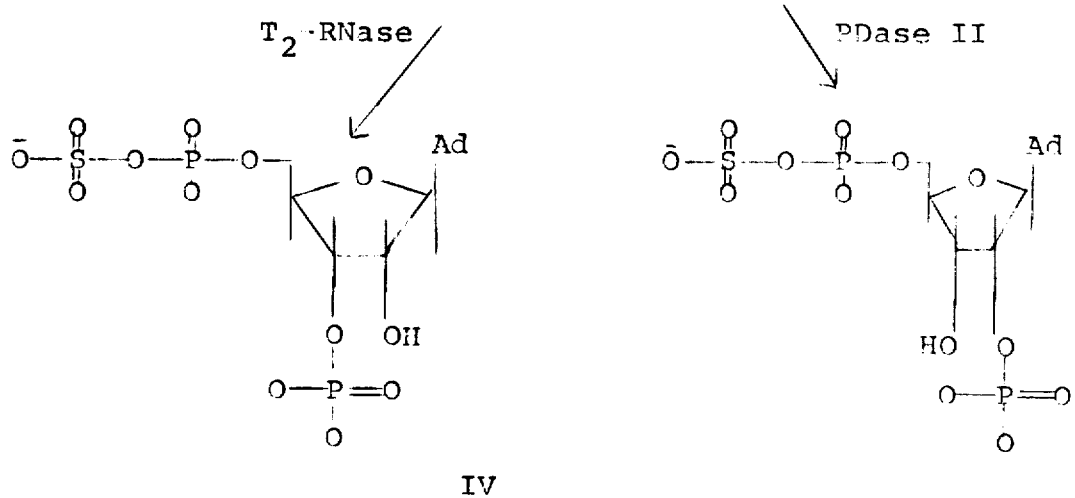

Signed and Sealed this

Eleventh Day of November 1980

[SEAL]

*Attest:*

*Attesting Officer*

SIDNEY A. DIAMOND
*Commissioner of Patents and Trademark*